(12) United States Patent
Giuberchio

(10) Patent No.: US 11,266,793 B2
(45) Date of Patent: Mar. 8, 2022

(54) SYRINGE WITH HIGH SAFETY IN USE

(71) Applicant: Aghetto S.r.l., Pavia (IT)

(72) Inventor: Carlo Giuberchio, Pavia (IT)

(73) Assignee: Aghetto S.r.l., Pavia (IT)

( * ) Notice: Subject to any disclaimer, the term of this patent is extended or adjusted under 35 U.S.C. 154(b) by 0 days.

(21) Appl. No.: 15/568,894

(22) PCT Filed: Apr. 22, 2016

(86) PCT No.: PCT/EP2016/059071
§ 371 (c)(1),
(2) Date: Oct. 24, 2017

(87) PCT Pub. No.: WO2016/170150
PCT Pub. Date: Oct. 27, 2016

(65) Prior Publication Data
US 2018/0099103 A1    Apr. 12, 2018

(30) Foreign Application Priority Data

Apr. 24, 2015 (IT) .......................... MI2015A000587

(51) Int. Cl.
*A61M 5/32* (2006.01)
*A61M 5/34* (2006.01)

(52) U.S. Cl.
CPC ........ *A61M 5/3276* (2013.01); *A61M 5/3202* (2013.01); *A61M 5/344* (2013.01); *A61M 5/347* (2013.01)

(58) Field of Classification Search
CPC .... A61M 5/3276; A61M 5/344; A61M 5/345; A61M 5/347; A61M 2005/3206;
(Continued)

(56) References Cited

U.S. PATENT DOCUMENTS 1,371,133 A * 3/1921 Valderrama ......... A61M 5/3129
604/218
1,373,669 A * 4/1921 Pittenger ............... A61M 5/282
604/192
(Continued)

FOREIGN PATENT DOCUMENTS

CN    1323638 A    11/2001
CN    1856335 A    11/2006
(Continued)

OTHER PUBLICATIONS

International Search Report dated Jul. 11, 2016 re: Application No. PCT/EP2016/059071; pp. 1-3; citing: US 2014/052078 A1, WO 2010/052517 A1 and EP 1 693 079 A1.
(Continued)

*Primary Examiner* — Kami A Bosworth
(74) *Attorney, Agent, or Firm* — McCarter & English, LLP; Beverly W. Lubit

(57) ABSTRACT

A syringe with high safety in use having a syringe body adapted to accommodate slidingly a plunger. The syringe body has a protruding end that is adapted to allow the mating of a base end of a needle. The syringe further includes elements for removing the needle and/or a cap interposed between the syringe body and the base end of the needle. The needle removal elements are adapted to be moved in a rotary direction for removal of the needle and/or the cap.

9 Claims, 2 Drawing Sheets

(58) Field of Classification Search
CPC ........ A61M 2005/3208; A61M 5/3204; A61M 5/3205; A61M 5/34; A61M 5/32
See application file for complete search history.

(56) References Cited

U.S. PATENT DOCUMENTS

| | | | | |
|---|---|---|---|---|
| 1,668,315 | A * | 5/1928 | Hein | A61M 5/344 285/238 |
| 1,683,350 | A * | 9/1928 | Hein | A61M 5/344 285/322 |
| 1,740,459 | A * | 12/1929 | Hein | A61M 5/344 604/242 |
| 1,742,497 | A * | 1/1930 | Dickinson | A61M 5/344 285/272 |
| 2,034,294 | A * | 3/1936 | Hein | A61M 5/344 604/241 |
| 3,638,650 | A * | 2/1972 | Burke | A61M 5/3202 604/240 |
| 4,629,455 | A * | 12/1986 | Kanno | A61M 5/344 285/332 |
| 4,747,835 | A | 5/1988 | Sandhaus | |
| 4,904,244 | A | 2/1990 | Harsh et al. | |
| 5,205,833 | A | 4/1993 | Harsh et al. | |
| 5,419,775 | A * | 5/1995 | Haffner | A61M 5/3135 604/187 |
| 5,624,402 | A * | 4/1997 | Imbert | A61M 5/3134 604/111 |
| 5,919,169 | A * | 7/1999 | Grams | A61M 5/344 604/240 |
| 6,371,319 | B2 | 4/2002 | Yeaton et al. | |
| 2003/0163093 | A1 * | 8/2003 | Thibault | A61M 5/344 604/241 |
| 2009/0143746 | A1 * | 6/2009 | Mudd | A61M 5/347 604/243 |
| 2012/0130351 | A1 * | 5/2012 | Alvain | A61M 5/344 604/533 |
| 2014/0025017 | A1 * | 1/2014 | Horita | A61M 5/344 604/241 |
| 2014/0052078 | A1 * | 2/2014 | Heinz | A61M 5/3134 604/241 |

FOREIGN PATENT DOCUMENTS

| | | |
|---|---|---|
| CN | 202236673 U | 5/2012 |
| CN | 106362244 A | 2/2017 |
| EP | 1693079 A1 | 8/2006 |
| JP | S5941429 A | 3/1984 |
| JP | S60129941 A | 7/1985 |
| JP | 1122753 U | 8/1989 |
| JP | 09117508 A2 | 5/1997 |
| JP | 11076277 A2 | 3/1999 |
| WO | 2010052517 A1 | 5/2010 |

OTHER PUBLICATIONS

Written Opinion dated Jul. 11, 2016 re: Application No. PCT/EP2016/059071; pp. 1-5; citing: US 2014/052078 A1 and WO 2010/052517 A1.
Office Action dated Feb. 10, 2020 re: Application No. 2017-555712, pp. 1-10, citing JP H11-076277, JPUH01-122753, JP H09-117508, JPU S59-41429 and JPU S60-129941.

* cited by examiner

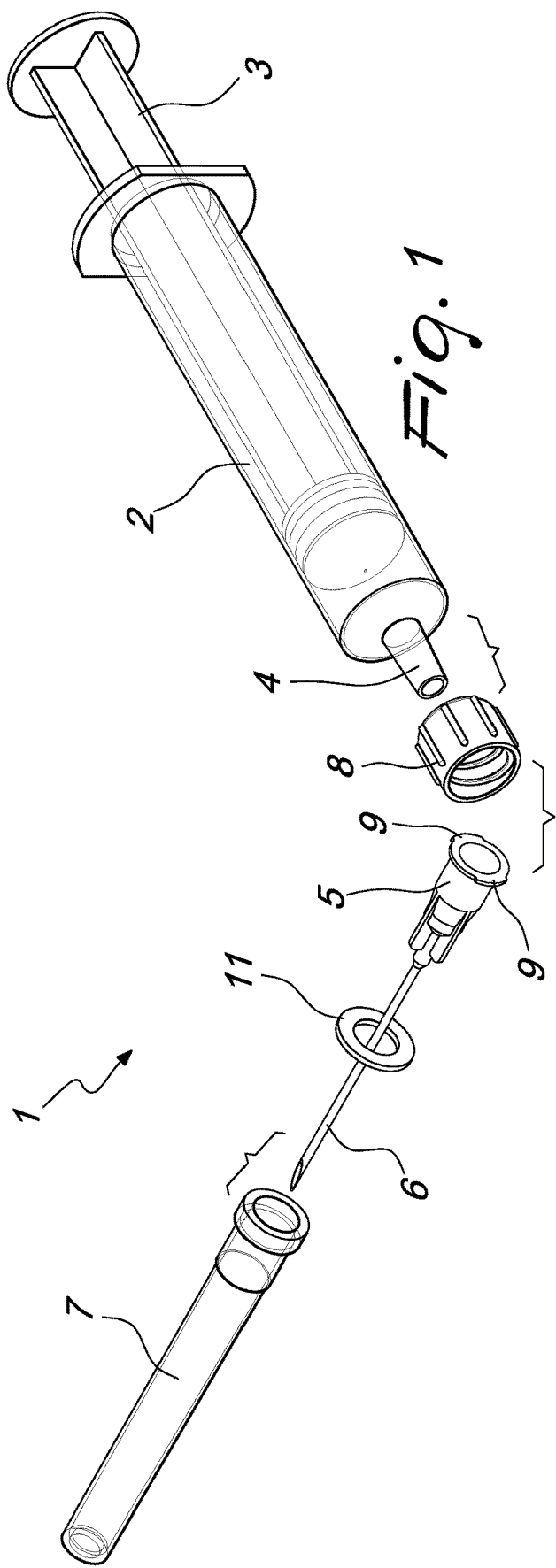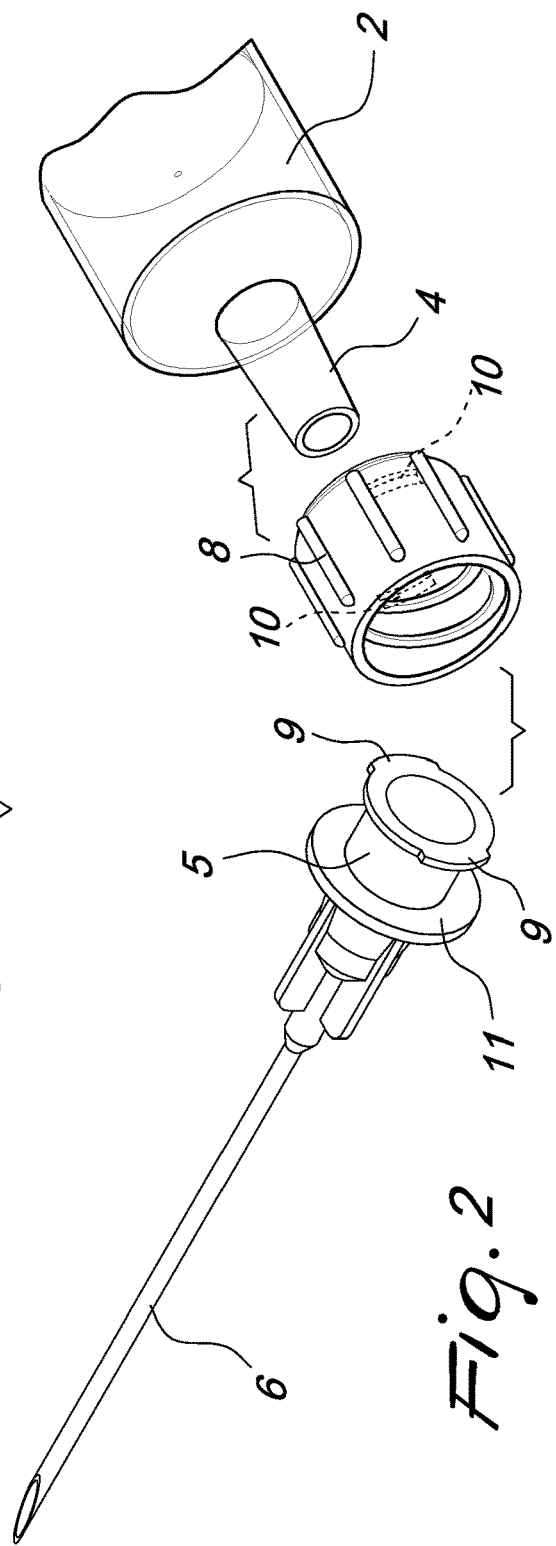

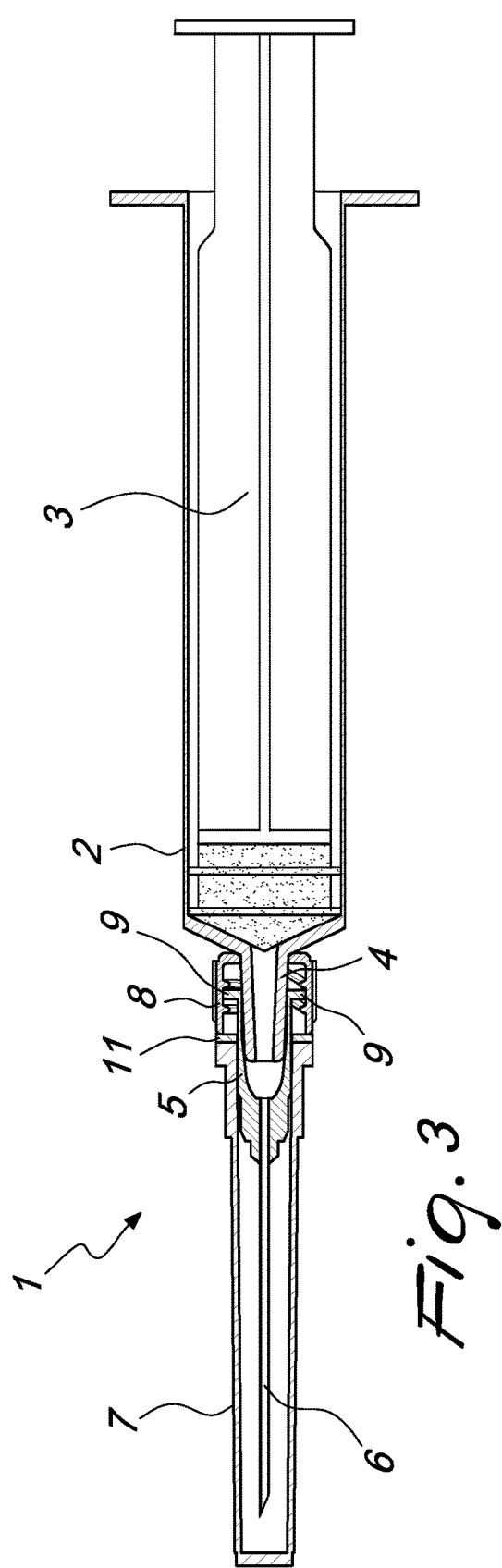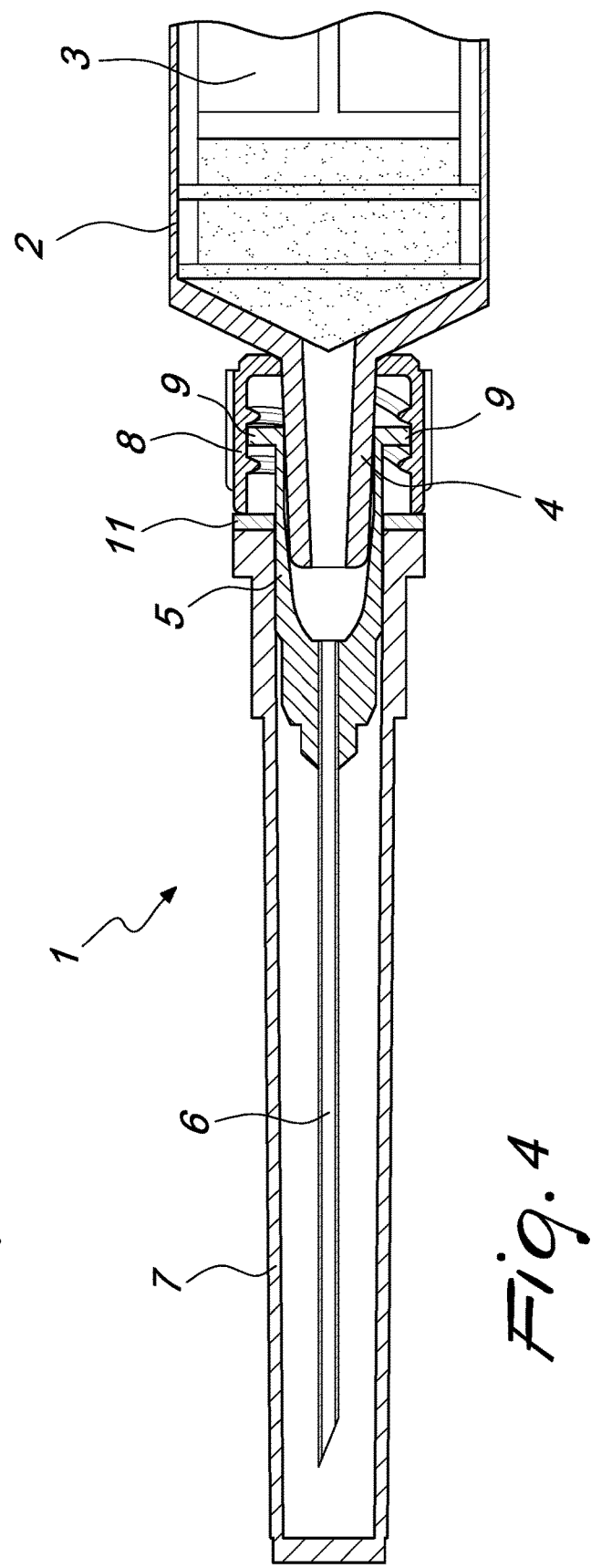

SYRINGE WITH HIGH SAFETY IN USE

TECHNICAL FIELD

The present disclosure relates to a syringe with high safety in use. More particularly, the disclosure relates to a syringe that has a device capable of removing the needle by using, on the part of the operator, a single hand, without the risk of accidentally injuring the operator by puncturing himself/herself with the tip of the needle.

BACKGROUND

As is known, currently, in order to be able to remove a needle from a syringe, the operator uses two hands, one to hold the body of the syringe and the other to remove the needle from such body.

First of all, it should be noted that it is not always possible to perform operations of this kind by using both hands and furthermore this operation is not absolutely practical from the point of view of effectiveness.

Another problem that can arise for the health operator is the need to remove the cap that protects the needle of the syringe in order to be able to perform an injection.

In this case, the health operator often finds himself/herself gripping the syringe with one hand and having the other hand busy. In this case, in order to be able to remove the cap from the needle, he/she must employ the aid of an assistant or is forced to grip the cap with his/her mouth and remove it from the syringe. This of course entails high safety risks.

SUMMARY

The aim of the present disclosure is to provide a syringe with high safety in use that allows the user to perform an operation for removing the needle and/or the associated cap by using a single hand.

Within this aim, the present disclosure provides a syringe with high safety in use, which allows the user to remove the needle and/or the cap of the needle in conditions of absolute safety, avoiding any accidental puncture.

The present disclosure further provides a syringe with high safety in use that is highly reliable, relatively simple to provide, and at competitive costs.

This aim, as well as these and other advantages that will become better apparent hereinafter, are achieved by providing a syringe with high safety in use, comprising a syringe body adapted to accommodate slidingly a plunger, the syringe body having a protruding end that is adapted to allow the mating of a base end of a needle, characterized in that it comprises means for removing the needle which are interposed between said syringe body and said base end of the needle, said needle removal means being adapted to be moved in a rotary direction for removal of the needle and/or of the protective cap of the needle.

BRIEF DESCRIPTION OF THE DRAWINGS

Further characteristics and advantages of the disclosure will become better apparent from the description of preferred but not exclusive embodiments of the syringe according to the present disclosure, illustrated by way of nonlimiting example in the accompanying drawings, wherein:

FIG. 1 is an exploded perspective view of a syringe according to the present disclosure;

FIG. 2 is an enlarged-scale partial exploded perspective view of FIG. 1;

FIG. 3 is a sectional view of the syringe according to the disclosure; and

FIG. 4 is an enlarged-scale partial sectional view of FIG. 3.

DETAILED DESCRIPTION OF THE DRAWINGS

With reference to FIGS. 1-4, the syringe according to the disclosure, designated generally by the reference numeral 1, comprises a syringe body 2 within which a plunger 3 slides. The body 2 ends, at one end, with a substantially frustum-like cross-section 4 adapted to accommodate the base end 5 of the needle 6, which is protected by a cap 7.

The syringe according to the disclosure has, between the body 2 of the syringe and the base end 5 of the needle 6, needle removal means 8 adapted to be rotated and to allow the removal of the needle 6 and/or of the cap 7.

In practice, the needle removal means 8 are constituted by a hollow tubular body that is adapted to be coupled to the end of the body 2 of the syringe, in particular to the portion 4 of such syringe, and to allow screwing or engagement of the base end 5 of the needle 6 therein.

Therefore, the needle 6 with its base end 5 can be screwed into the body 8 or can be interlocked by means of wings 9 of the base end 5 of the needle 6 that engage in corresponding slots 10 defined in the tubular body 8 that constitutes the means for removing the needle 6.

It is possible to provide, between the tubular body 8 and the base end 5 of the needle 6, a washer 11 that allows the tubular body 8 to abut against the cap 7 of the needle so as to disconnect it from the needle.

The diameter of the hole of the tubular body 8 directed toward the body 2 of the syringe is equal to, or greater than, the diameter of the hole of the base end 5 of the needle.

In an alternative embodiment, the tubular body 8 can be shaped so as to slide on the body 2 of the syringe instead of being connected to its end 4.

Use of the syringe according to the disclosure is as follows.

The operator, by gripping with a single hand the tubular body 8, which can slide on the end part of the body 2 of the syringe, and by turning it with his/her fingers, causes the needle inserted on the end part of the body of the syringe to perform a rotary motion so that it can disconnect easily from the syringe.

If the tubular body 8 also abuts against the cap 7 of the needle, for example by way of the interposition of the washer 11, the operator can remove the cap of the needle by using a single hand. If the washer 11 is present, once the tubular body 8 has been moved, the washer 11 abuts against the base of the cap 7 and removes it.

If the tubular body 8 is screwed onto the base of the needle and can allow the removal of the cap of the needle by moving it (screwing it on) on the base of the needle, it abuts against the end of the cap 7 of the syringe and disconnects it from the needle.

If the tubular body 8 is screwed onto the base of the needle and can allow the removal of the cap of the needle or of the needle by moving it (screwing it on) on the base of the needle, it initially abuts against the end of the cap 7 of the syringe and disconnects it from the needle 7 and then, by continuing to screw it on, the tubular body 8 reaches the end of its stroke. At this point the operator, by continuing to screw on the tubular body, can make the needle 6 perform a rotary motion on the protruding end part of the syringe that will allow him/her to disconnect easily the needle 6, together with the tubular body, from the syringe (remove the tubular body 8 and the needle 6 from the syringe together).

The operator, by gripping alternately with a single hand the tubular body 8 that can slide on the end part of the body 2 of the syringe and by turning it with his/her fingers, once the tubular body has abutted against the end part of the syringe, by continuing to turn it causes, if the tubular body is long enough, the needle fitted on the end part of the body of the syringe to be pushed outwardly until it disconnects from the syringe.

In practice it has been found that the syringe according to the present disclosure achieves fully the intended advantages and features, since it allows to remove the needle and/or its cap by using a single hand without the risk of accidental punctures.

The syringe thus conceived is susceptible of numerous modifications and variations.

All the details may further be replaced with other technically equivalent elements.

In practice, the materials used, as well as the contingent shapes and dimensions, may be any according to requirements and to the state of the art.

The invention claimed is:

1. A syringe, comprising:
   a syringe body adapted to accommodate slidingly a plunger, the syringe body having a protruding end;
   a needle including a base end, the needle adapted to be mated on the protruding end of the syringe body;
   a cap of the needle; and
   removal means for removing the needle and the cap, the removal means adapted to slide on the protruding end of the syringe body;
   wherein the base end of the needle is adapted to engage with the removal means;
   wherein the removal means is adapted to be interposed between the syringe body and the base end of the needle when the base end of the needle is mated to the protruding end; and
   wherein the removal means is adapted to move in a rotary direction for removal of the needle and the cap from the syringe body, a rotation of the removal means causing an abutment of the removal means against the cap, disconnecting the cap from the needle, and continued rotation of the removal means disconnecting the needle with the removal means from the syringe body.

2. The syringe according to claim 1, wherein the removal means includes a tubular body adapted to be mated to the protruding end of the syringe body and to allow engagement of the base end of the needle in the tubular body.

3. The syringe according to claim 2, wherein the tubular body allows for screwing of the base end of the needle into the tubular body of the removal means.

4. The syringe according to claim 2, wherein a diameter of a hole of the tubular body directed toward the syringe body is equal to, or greater than, a diameter of a hole of the base end of the needle that is adapted to be connected to the protruding end.

5. The syringe according to claim 2, wherein the tubular body includes slots adapted to allow for engagement with wings defined at the base end of the needle.

6. The syringe according to claim 1, comprising a washer disposed between the removal means and the base end of the needle.

7. The syringe according to claim 6, wherein rotation of the removal means causes an abutment of the washer against a base of the cap to disconnect the cap from the needle.

8. The syringe according to claim 1, wherein continued rotation of the removal means results in the removal means reaching an end of its stroke, which results in disconnection of the needle with the removal means from the syringe body.

9. A syringe, comprising:
   a syringe body adapted to accommodate slidingly a plunger, the syringe body having a protruding end;
   a needle including a base end, the needle adapted to be mated on the protruding end of the syringe body;
   a cap of the needle; and
   a removal body for removing the needle and the cap, the removal body adapted to slide on the protruding end of the syringe body;
   wherein the base end of the needle is adapted to engage with the removal body;
   wherein the removal body is adapted to be interposed between the syringe body and the base end of the needle when the base end of the needle is mated to the protruding end; and
   wherein the removal body is adapted to move in a rotary direction for removal of the needle and the cap from the syringe body, a rotation of the removal body causing an abutment of the removal means against the cap, disconnecting the cap from the needle, and continued rotation of the removal body disconnecting the needle with the removal body from the syringe body.

* * * * *